US006976521B2

(12) United States Patent
Mlinar et al.

(10) Patent No.: US 6,976,521 B2
(45) Date of Patent: Dec. 20, 2005

(54) APPARATUS FOR ASSEMBLING REFASTENABLE ABSORBENT GARMENTS

(75) Inventors: Joseph A. Mlinar, Appleton, WI (US); Jesse P. Sorenson, Little Chute, WI (US); Kenneth J. Wagner, Greenville, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 10/756,013

(22) Filed: Jan. 13, 2004

(65) Prior Publication Data

US 2004/0144496 A1    Jul. 29, 2004

Related U.S. Application Data

(62) Division of application No. 09/954,480, filed on Sep. 14, 2001, now Pat. No. 6,682,626.

(51) Int. Cl.[7] .............................................. B32B 35/00
(52) U.S. Cl. ....................... 156/519; 156/522; 156/512; 156/552; 156/302; 156/252; 156/265; 156/270
(58) Field of Search ............................... 156/252, 253, 156/265, 270, 302, 519, 522

(56) References Cited

U.S. PATENT DOCUMENTS

| 3,663,962 | A | 5/1972 | Burger |
| 3,828,367 | A | 8/1974 | Bourgeois |
| 3,874,032 | A | 4/1975 | Simon et al. |
| 4,409,052 | A | 10/1983 | von Agris et al. |
| 4,608,115 | A | 8/1986 | Schroth et al. |
| 4,615,695 | A | 10/1986 | Cooper |
| 4,647,336 | A | 3/1987 | Coenen et al. |
| 4,650,530 | A | 3/1987 | Mahoney et al. |
| D290,780 | S | 7/1987 | Wistrand |
| 4,713,132 | A | 12/1987 | Abel et al. |
| 4,743,241 | A | 5/1988 | Igaue et al. |
| 4,758,293 | A | 7/1988 | Samida |
| 4,801,298 | A | 1/1989 | Sorenson et al. |
| 4,847,134 | A | 7/1989 | Fahrenkrug et al. |
| 4,906,243 | A | 3/1990 | Dravland |
| 4,960,414 | A | 10/1990 | Meyer |

(Continued)

FOREIGN PATENT DOCUMENTS

DE        198 13 334 A1    9/1999

(Continued)

OTHER PUBLICATIONS

U.S. Appl. No. 09/954,444, entitled "Method and Apparatus for Assembling Refastenable Absorbent Garments," filed on Sep. 14, 2001 (659-876).

(Continued)

Primary Examiner—Linda Gray
(74) Attorney, Agent, or Firm—Brinks Hofer Gilson & Lione

(57) ABSTRACT

An apparatus for fabricating the refastenable absorbent garment includes a web perforator adapted to perforate a base web in a cross direction and a construction drum positioned downstream of the web perforator and adapted to receive the perforated base web. A landing material cutter is adapted to cut a landing material and fastener material in the cross direction. A landing member rotator is positioned adjacent the construction drum and downstream of the landing material cutter. The landing member rotator is adapted to separate successive pieces of the landing material with the fastener material attached thereto at the cross direction landing material cut, rotate the pieces of landing material with the fastener member attached thereto and apply the piece of landing material and fastener material to the base web on the construction drum.

18 Claims, 4 Drawing Sheets

U.S. PATENT DOCUMENTS

| | | | |
|---|---|---|---|
| 4,998,929 A | 3/1991 | Bjorksund et al. | |
| 5,080,741 A | 1/1992 | Nomura et al. | |
| 5,087,253 A | 2/1992 | Cooper | |
| 5,096,532 A | 3/1992 | Neuwirth et al. | |
| 5,110,403 A | 5/1992 | Ehlert | |
| 5,145,351 A | 9/1992 | Rossi | |
| 5,147,487 A | 9/1992 | Nomura et al. | |
| 5,221,390 A | 6/1993 | Persson et al. | |
| 5,235,515 A | 8/1993 | Ungpiyakul et al. | |
| 5,242,436 A | 9/1993 | Weil et al. | |
| 5,286,543 A | 2/1994 | Ungpiyakul et al. | |
| 5,340,424 A | 8/1994 | Matsushita | |
| 5,370,634 A | 12/1994 | Ando et al. | |
| 5,376,198 A | 12/1994 | Fahrenkrug et al. | |
| 5,399,219 A * | 3/1995 | Roessler et al. | 156/259 |
| 5,415,649 A | 5/1995 | Watanabe et al. | |
| 5,449,353 A | 9/1995 | Watanabe et al. | |
| 5,454,803 A | 10/1995 | Sageser et al. | |
| 5,500,063 A | 3/1996 | Jessup | |
| 5,540,796 A | 7/1996 | Fries | |
| 5,542,943 A | 8/1996 | Sageser | |
| 5,552,007 A | 9/1996 | Rajala et al. | |
| 5,552,013 A | 9/1996 | Ehlert et al. | |
| 5,554,145 A | 9/1996 | Roe et al. | |
| 5,556,504 A | 9/1996 | Rajala et al. | |
| 5,562,790 A | 10/1996 | Ehlert et al. | |
| 5,569,234 A | 10/1996 | Buell et al. | |
| 5,582,606 A | 12/1996 | Bruemmer et al. | |
| 5,591,155 A | 1/1997 | Nishikawa et al. | |
| 5,601,547 A | 2/1997 | Kato et al. | |
| 5,609,702 A | 3/1997 | Andersen | |
| 5,624,420 A | 4/1997 | Bridges et al. | |
| 5,643,377 A | 7/1997 | Juergens | |
| 5,643,396 A | 7/1997 | Rajala et al. | |
| 5,659,229 A | 8/1997 | Rajala | |
| 5,660,657 A | 8/1997 | Rajala et al. | |
| 5,660,679 A | 8/1997 | Rajala et al. | |
| 5,667,608 A | 9/1997 | Rajala et al. | |
| 5,683,376 A | 11/1997 | Kato et al. | |
| 5,685,873 A | 11/1997 | Bruemmer | |
| 5,685,874 A | 11/1997 | Buell et al. | |
| RE35,687 E | 12/1997 | Igaue et al. | |
| 5,707,364 A | 1/1998 | Coates | |
| 5,707,470 A | 1/1998 | Rajala et al. | |
| 5,711,832 A | 1/1998 | Glaug et al. | |
| 5,711,847 A | 1/1998 | Rajala et al. | |
| 5,716,478 A | 2/1998 | Boothe et al. | |
| 5,733,411 A | 3/1998 | Bett | |
| 5,745,922 A | 5/1998 | Rajala et al. | |
| 5,749,866 A | 5/1998 | Roe et al. | |
| 5,749,989 A | 5/1998 | Linman et al. | |
| 5,759,340 A | 6/1998 | Boothe et al. | |
| 5,766,389 A | 6/1998 | Brandon et al. | |
| 5,817,199 A | 10/1998 | Brennecke et al. | |
| 5,836,931 A | 11/1998 | Toyoda et al. | |
| 5,855,574 A | 1/1999 | Kling et al. | |
| 5,858,151 A | 1/1999 | Igaue et al. | |
| 5,858,515 A | 1/1999 | Stokes et al. | |
| 5,879,500 A | 3/1999 | Herrin et al. | |
| 5,897,545 A | 4/1999 | Kline et al. | |
| 5,904,673 A | 5/1999 | Roe et al. | |
| 5,940,887 A | 8/1999 | Rajala et al. | |
| 5,957,908 A | 9/1999 | Kline et al. | |
| 6,022,431 A | 2/2000 | Blenke et al. | |
| 6,022,432 A | 2/2000 | Elsberg et al. | |
| 6,036,805 A | 3/2000 | McNichols | |
| 6,077,379 A | 6/2000 | Herrin et al. | |
| 6,098,203 A | 8/2000 | Rajala et al. | |
| 6,113,717 A | 9/2000 | Vogt et al. | |
| 6,132,410 A | 10/2000 | Van Gompel et al. | |
| 6,132,411 A | 10/2000 | Huber et al. | |
| 6,139,004 A | 10/2000 | Couillard et al. | |
| 6,197,138 B1 | 3/2001 | McNichols | |
| 6,210,388 B1 | 4/2001 | Widlund et al. | |
| 6,217,563 B1 | 4/2001 | Van Gompel et al. | |
| 6,217,690 B1 | 4/2001 | Rajala et al. | |
| 6,227,541 B1 | 5/2001 | Couillard et al. | |
| 6,240,569 B1 | 6/2001 | Van Gompel et al. | |
| 6,264,641 B1 | 7/2001 | Van Gompel et al. | |
| 6,328,725 B2 | 12/2001 | Fernfors | |
| 6,336,922 B1 | 1/2002 | Van Gompel et al. | |
| 6,361,527 B1 | 3/2002 | Van Gompel et al. | |
| 6,375,646 B1 | 4/2002 | Widlund et al. | |
| 6,478,786 B1 | 11/2002 | Glaug et al. | |
| 6,481,362 B2 | 11/2002 | Hietpas et al. | |
| 6,730,189 B1 * | 5/2004 | Franzmann et al. | 156/265 |
| 2001/0042584 A1 | 11/2001 | Karami et al. | |
| 2003/0075277 A1 * | 4/2003 | Vogt et al. | 156/519 |

FOREIGN PATENT DOCUMENTS

| | | |
|---|---|---|
| EP | 0528 282 A2 | 2/1993 |
| EP | 0 570 980 | 11/1993 |
| EP | 0 591 647 B1 | 4/1994 |
| EP | 0 630 221 B2 | 12/1994 |
| EP | 0 719 534 B1 | 7/1996 |
| EP | 0 934 739 A2 | 8/1999 |
| EP | 0 396 512 A2 | 11/1999 |
| EP | 1 013 251 A1 | 6/2000 |
| EP | 1 062 930 A2 | 12/2000 |
| EP | 1 066 811 | 1/2001 |
| EP | 0 907 510 B1 | 3/2002 |
| GB | 2 288 316 | 11/1997 |
| GB | 2 311 249 | 7/1999 |
| JP | 03176053 A | 7/1991 |
| JP | 3-205053 | 9/1991 |
| JP | 4-22359 | 1/1992 |
| WO | WO 95/22306 | 8/1995 |
| WO | WO 95/27461 | 10/1995 |
| WO | WO 95/27462 | 10/1995 |
| WO | WO 96/14039 | 5/1996 |
| WO | WO 96/23466 | 8/1996 |
| WO | WO 96/23467 | 8/1996 |
| WO | WO 96/38112 | 12/1996 |
| WO | WO 97/02795 | 1/1997 |
| WO | WO 97/02797 | 1/1997 |
| WO | WO 97/02799 | 1/1997 |
| WO | WO 97/23180 | 7/1997 |
| WO | WO 97/46197 | 12/1997 |
| WO | WO 97/48357 | 12/1997 |
| WO | WO 98/27921 | 7/1998 |
| WO | WO 99/33425 | 7/1999 |
| WO | WO 00 20208 | 4/2000 |
| WO | WO 00/37009 | 6/2000 |
| WO | WO 01/13843 | 3/2001 |
| WO | WO 01/13844 | 3/2001 |
| WO | WO 01/13845 | 3/2001 |
| WO | WO 01/13846 | 3/2001 |
| WO | WO 01/13847 | 3/2001 |
| WO | WO 01/13848 | 3/2001 |
| WO | WO 01/13849 | 3/2001 |
| WO | WO 01/13850 | 3/2001 |
| WO | WO 01/13851 | 3/2001 |
| WO | WO 01/43682 A1 | 6/2001 |
| WO | WO 02/083048 A1 | 10/2002 |
| WO | WO 02/083049 A1 | 10/2002 |

OTHER PUBLICATIONS

U.S. Appl. No. 09/954,478 entitled "Method and Apparatus for Assembling Refastenable Absorbent Garments," filed Sep. 14, 2001 (659-874).

U.S. Appl. No. 09/954,480 entitled "Method and Apparatus for Assembling Refastenable Absorbent Garment," filed Sep. 14, 2001 (659-878).
U.S. Appl. No. 09/637,432 entitled "Refastenable Absorbent Articel Exhibiting Improved Body Fit," filed on Aug. 11, 2000 (KC 16098).
U.S. Appl. No. 09/637,430 entitled "Refastenable Absorbent Article Exhibiting Improved Body Fit," filed Aug. 11, 200 (KC 16099).
U.S. Appl. No. 09/637,431 entitled "Refastenable Absorbent Article Exhibiting Improved Body Fit," filed Aug. 11, 2000 (KC 16100).
U.S. Appl. No. 09/637,429 entitled "Absorbent Article Having a Refastenable Mechanism," filed Aug. 11, 2000 (KC 16101).
U.S. Appl. No. 09/637,428 entitled "Absorbent Article Having a Refastenable Mechanism," filed Aug. 11, 2000 (KC 16102).
U.S. Appl. No. 09/637,427 entitled "Absorbent Article Having a Refastenable Mechanism," filed Aug. 11, 2000 (KC 16103).
U.S. Appl. No. 09/637,423 entitled Absorbent Article Having a Refastenable Mechanism, filed Aug. 11, 2000 (KC 16104).
U.S. Appl. No. 09/637,424 entitled "Absorbent Article Having a Refastenable Mechanism," filed Aug. 11, 2000 (KC 16105).
U.S. Appl. No. 09/637,425 entitled "Absorbent Article Having a Refastenable Mechanism," filed Aug. 11, 2000 (KC 16106).
U.S. Appl. No. 09/637,426 entitled "Absorbent Article Exhibiting Improved Body Fit," filed Aug. 11, 2000 (KC 16107).
U.S. Patent Application entitled "Methods of Changing Size of Pant-Type Personal Care Articles Outputted From a Manufacturing Process," filed Apr. 13, 2001 (14755).
U.S. Appl. No. 09/834,869 entitled "Pant-Type Personal Care Articles, and Methods of Making and Using Such Personal Care Articles," filed Apr. 13, 2001 (KC 14754).
U.S. Appl. No. 09/834,870 entitled "Passive Bonds for Personal Care Article," filed Apr. 13, 2001 (KC 15412).
U.S. Appl. No. 09/834,870 entitled "Multiple Component Web," filed Apr. 13, 2001 (KC 15649).
U.S. Appl. No. 09/834,875 entitled "Method of Assembling Personal Care Absorbent Article," filed Apr. 13, 2001 (KC 15490).
U.S. Provisional Appl. No. 60/150,382 entitled "Pants, Refastenable Pants/Undergarments/Briefs Product Design and Process for Manufacturing on a Single Asset," filed Aug. 23, 1999 (KC 14509).
U.S. Provisional Appl. No. 60/150,327 entitled "Refastenable Pant with Perforated Front Panels," filed Aug. 23, 1999 (KC 14647).
U.S. Appl. No. 09/002,020 entitled "Personal Care Article Having a Stretch Outer Cover and Non-Stretch Grasping Panels," filed Dec. 31, 1997 (KC 12221).
International Search Report in corresponding PCT Application No. PCT/US02/19320, dated Jul. 3, 2003, 5 pages.

* cited by examiner

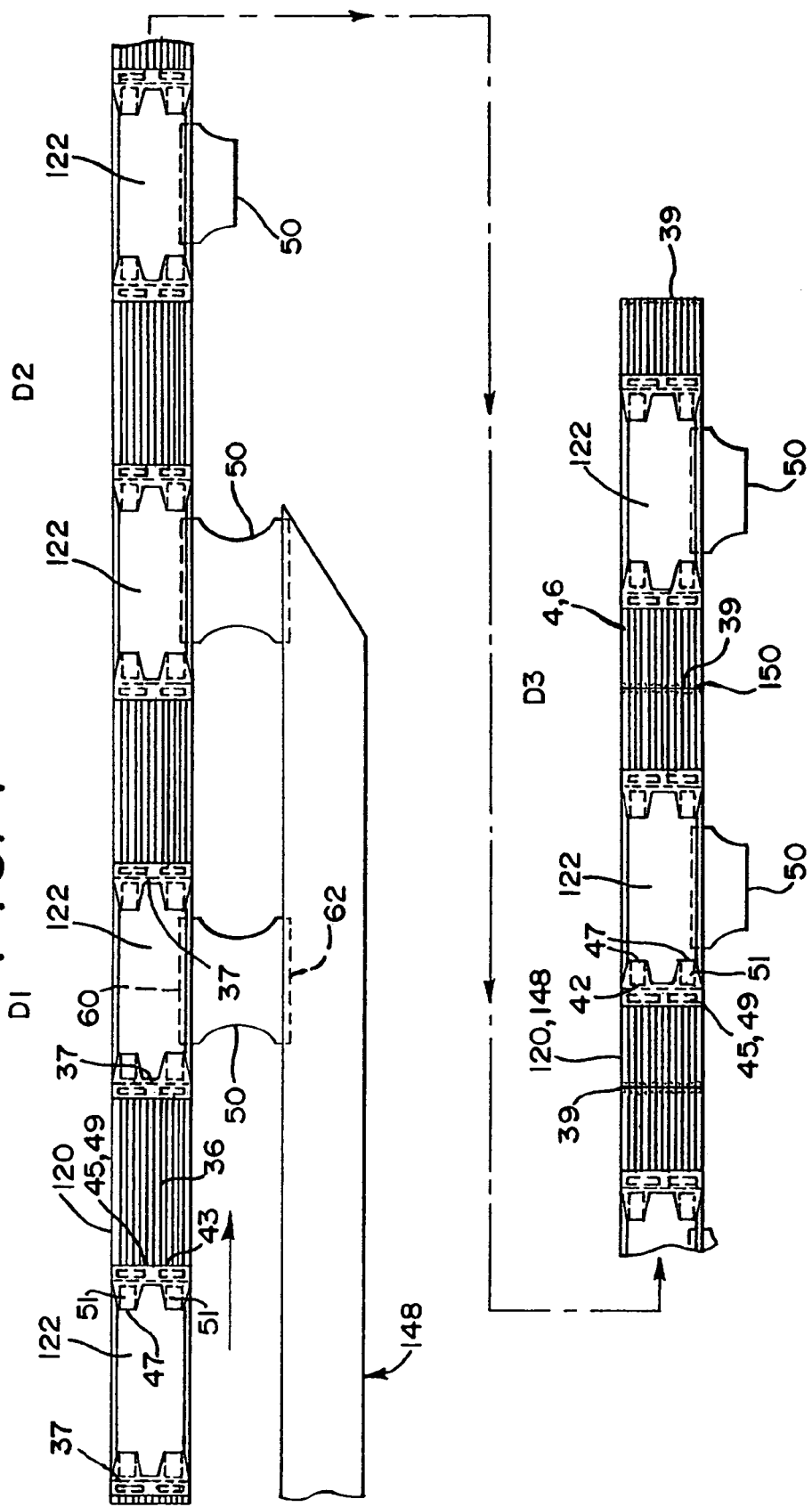

APPARATUS FOR ASSEMBLING REFASTENABLE ABSORBENT GARMENTS

This application is a division of U.S. application Ser. No. 09/954,480, filed Sep. 14, 2001, now issued as U.S. Pat. No. 6,682,626, the entire disclosure of which is hereby incorporated herein by reference.

BACKGROUND

The present invention relates generally to a refastenable absorbent garment, and in particular, to a method and apparatus for assembling a refastenable absorbent garment having a fastener that refastenably engages a landing member.

Absorbent garments can be configured in many different forms. For example, absorbent garments can be configured as a pant-type, pull-on garment, or as a diaper-type product that is drawn up between the legs and fastened about the waist with various fastening systems. Pant-type, pull-on garments are often provided with various elastic elements that can conform to the body of the user and provide a comfortable, snug fit. Such garments, however, often do not have a refastenable mechanism that allows the garment to be easily removed after use or to be adjusted during use.

On the other hand, diaper-type products, which can be configured with fastening systems that allow the user to detach and reattach various fasteners so as to provide a refastenable absorbent garment, often are not configured with various elastic elements, for example around the waist, and may not conform well to the body of the user and/or may provide a bulky appearance beneath the user's garments. Moreover, such garments are typically produced as an "open" product, which is open at the sides and which cannot be pulled on like a pant-type garment. Some users prefer a pull-on type garment, since the garment is applied to the user like conventional underwear. Therefore, there remains a need for an improved absorbent garment, and in particular a pant-type garment, that is refastenable and provides a snug fit with a non-bulky appearance.

In addition, manufacturing facilities are often configured to fabricate one particular type of product. As such, these facilities may not provide the flexibility to transition between fabricating a pull-on type garment and fabricating a refastenable, pull-on type garment using a single manufacturing line or asset. Therefore the need also remains for improved methods and assemblies for manufacturing refastenable absorbent garments.

SUMMARY

Briefly stated, in one aspect, the invention is directed to a method for assembling a refastenable absorbent garment. The method comprises moving a landing material in a machine direction, wherein the landing material has opposite lateral side edges, moving a fastener material in a machine direction, wherein the fastener material comprises a refastenable portion and a base portion, and removeably attaching the refastenable portion of the fastener material to at least one of the side edges of the landing material. The method preferably further includes successively cutting the landing material with the fastener material removeably attached thereto along a cross direction and thereby forming a plurality of landing members with a fastener member removeably attached thereto and successively rotating each of the plurality of landing members with the fastener member removeably attached thereto. In one preferred embodiment, the landing member with the fastener member removeably attached thereto is rotated approximately 90 degrees. The method preferably further includes moving a base web in a machine direction, successively attaching each of the landing members to the base web and attaching the base portion of the fastener member to the base web.

In one preferred embodiment of the invention, the method further comprises moving a pair of strips of fastener material in a machine direction and attaching the strips to the opposite lateral side edges of the landing material. In another preferred embodiment, the method further comprises applying an adhesive to the base web, and placing elastic strands on the base web along the machine direction.

In yet another preferred embodiment, the method further comprises cutting the base web along a cross direction and attaching the landing member and fastener member to the base web on opposite sides of the cross direction cut. In one preferred embodiment, the cross direction cut is formed as a perforation.

In another aspect of the invention, an apparatus for fabricating a refastenable absorbent garment includes a web perforator adapted to perforate the base web in a cross direction and a construction drum positioned downstream of the web perforator and adapted to receive the base web. The apparatus also preferably includes a landing material cutter adapted to cut the landing material and fastener material in the cross direction, and a landing member rotator positioned adjacent the construction drum. The landing member rotator is adapted to separate successive pieces of the landing material with the fastener material attached thereto at the cross direction landing material perforation, rotate the pieces of landing material with the fastener member attached thereto and apply the landing member and fastener member to the base web on the construction drum.

The present invention provides significant advantages over other absorbent garments and methods and apparatus for the manufacture thereof. For example, in one embodiment of a pant-type garment, the user can pull the garment on or off like underwear. However, by making the absorbent garment refastenable, it can be applied without needing to pull the garment on or off like a pant-like garment, if desired. For example, the garment can be pulled on like a pant-type garment, and removed like a diaper-type product by disengaging the fastener members and breaking the lines of weakness. Alternatively, the garment can be pulled on and off like a pant-like garment, and can thereafter be converted to a refastenable garment, if desired. For example, the garment can be made bigger or smaller simply by adjusting the positioning of the fasteners. Moreover, in one particular application, wherein the garment is used by adults, for example with occasional incontinence problems, the garment can be pulled up or down by the user, or the fastening system may be disengaged and engaged repeatedly by the user while the garment remains unsoiled over an extended period of time.

In one preferred embodiment, the absorbent garment includes elastic elements extending along the waist region. The elastic elements provide a snug, comfortable fit that does not create a bulky appearance beneath the user's outer garments. The combination of the refastenable fasteners with the elastic elements further enhances the fit and appearance of the garment.

At the same time, the separate assembly of a refastenable subassembly, comprising a landing member and at least one fastener removeably secured thereto, allows the manufacturer to switch easily between making a non-refastenable, pant-type product and a refastenable, pant-type product. In particular, the process of rotating the refastenable subassembly and attaching it to the base web can be omitted if desired.

In addition, the fabrication of the refastenable subassembly is greatly simplified by removeably attaching the refastenable portion of the fastener material to the landing material, preferably without any other bonds or fasteners disposed therebetween. In this way, the refastening mechanism, and in particular the interface between the refastenable portion and the landing material, which provides flexibility to the user when wearing the absorbent garment, also provides a simple and efficient way to maintain the position and relationship between the fastener member and the landing member during the manufacturing process. As such, the cost of the system and its operation can be minimized.

The present invention, together with further objects and advantages, will be best understood by reference to the following detailed description taken in conjunction with the accompanying drawings.

BRIEF DESCRIPTION OF THE DRAWINGS

FIG. 4 is a schematic top view representation of a method of fabricating a refastenable absorbent garment.

DETAILED DESCRIPTION OF THE PRESENTLY PREFERRED EMBODIMENTS

Figure 1:
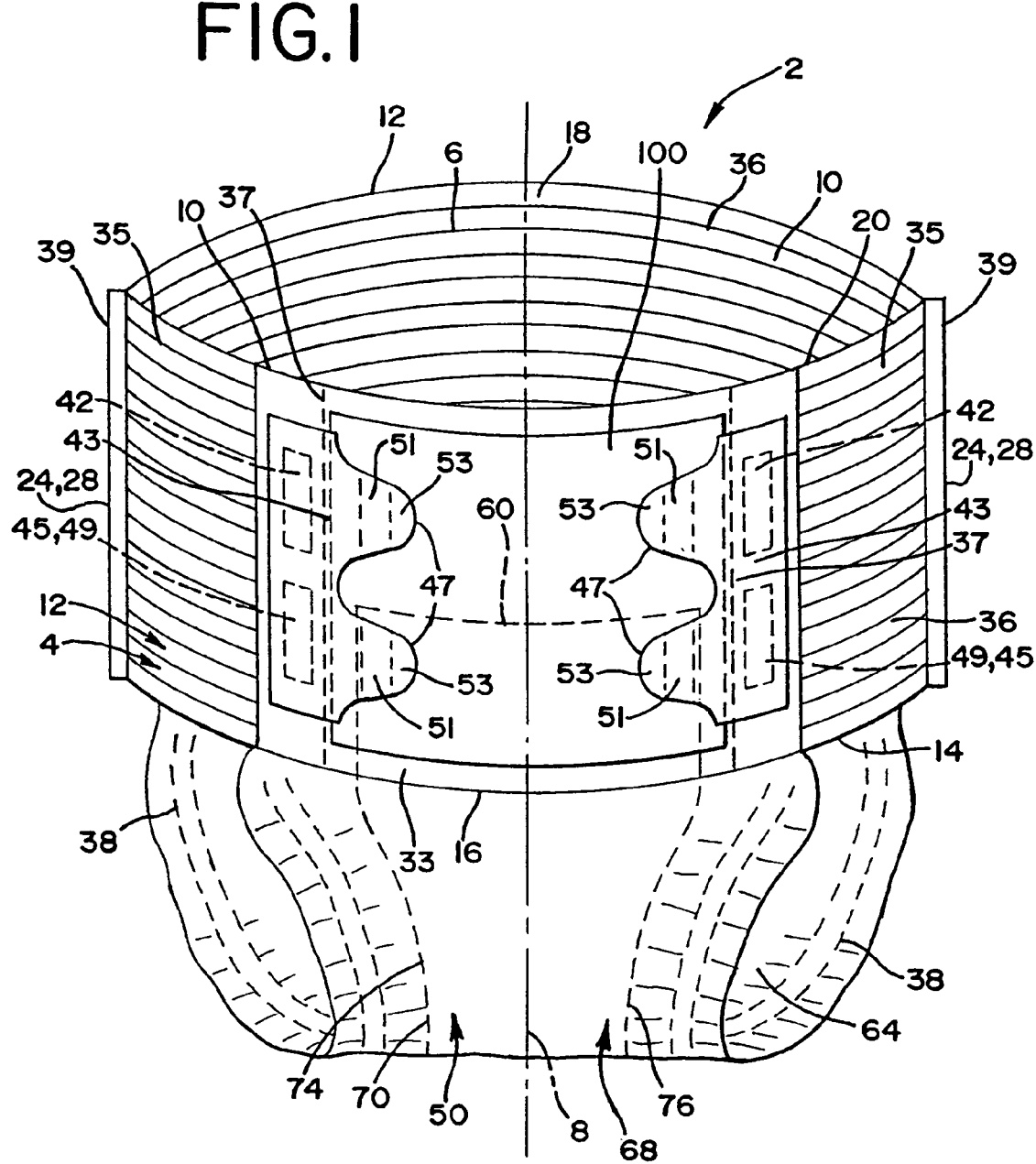
FIG. 1 is a perspective view of one embodiment of a refastenable absorbent garment in a fastened configuration.

It should be understood that the term "longitudinal," as used herein, means of or relating to length or the lengthwise direction, and in particular, the direction running between the front and back of the user. The term "laterally," as used herein means situated on, directed toward or running from side to side, and in particular, a direction running from the left to the right of a user, and vice versa. The terms "upper," "lower," "inner," and "outer" as used herein are intended to indicate the direction relative to the user wearing an absorbent garment over the crotch region, while the terms "inboard" and "outboard" refer to the directions relative to a centerline 8 of the garment. For example, the terms "inner" and "upper" refer to a "bodyside," which means the side closest to the body of the user, while the terms "outer" and "lower" refer to a "garment side."

The term "bodyside" should not be interpreted to mean in contact with the body of the user, but rather simply means the side that would face toward the body of the user, regardless of whether the absorbent garment is actually being worn by the user and regardless of whether there are or may be intervening layers between the component and the body of the user. Likewise, the term "garment side" should not be interpreted to mean in contact with the garments of the user, but rather simply means the side that faces away from the body of the user, and therefore toward any outer garments that may be worn by the user, regardless of whether the absorbent garment is actually being worn by a user, regardless of whether any such outer garments are actually worn and regardless of whether there may be intervening layers between the component and any outer garment.

The term "machine direction" means the direction of flow as the various members and webs progress along the fabrication line and process. It should be understood that various separate members or webs can each be traveling in a machine direction, but with the various machine directions not necessarily being parallel or oriented in the same direction. For example, one web may be traveling a first machine direction, which is substantially perpendicular to the travel of another web in a second machine direction.

The term "cross direction" means the direction substantially perpendicular to the machine direction.

The term "downstream" means that one item is positioned more closely to the output or finished product end of the machine and/or process relative to another item. Conversely, the term "upstream" means that an item is positioned more closely to the input end of the machine or process relative to another item. For example, the output end is downstream of the input end, and vice versa, the input end is upstream of the output end.

The phrases "removeably attached," "removeably attaching," "removeably connected," "removeably engaged," "releasably attached," "releasably connected," or "releasably engaged," and variations thereof, refers to two or more elements being connected or connectable such that the elements tend to remain connected absent a separation force applied to one, both or all of the elements, and where the elements are capable of being separated upon the application of a separation force. The required separation force is typically beyond that encountered while wearing the absorbent garment.

The phrases "fixedly secured," "fixedly engaged," "fixedly attached," "fixedly connected," and variations thereof, refers to two or more elements being connected or connectable such that they are not disconnected or otherwise separated, and are not intended to be separated or disconnected, during the normal operation and use of the absorbent garment.

The term "web" refers to a continuous stream of material, whether made from one or more layers or substrates, and regardless of whether it may have non-continuous, discrete items disposed thereon.

Referring to FIG. 1, an absorbent garment 2 includes a first, front body panel 4 and a second, rear body panel 6. The term "body panel" refers to the portion(s) of the absorbent garment, whether made of one or more layers or substrates or of one or more pieces or components, that is/are fitted circumferentially around at least the waist region of the user, including for example the user's lower back, buttock, hips and abdomen. The first and second body panels each have an inner, bodyside surface 10 and an outer, garment side surface 12. The first, front body panel 4 has a length, which is measured between opposed first and second terminal edges 16 and 20, and which is less than the overall length of the absorbent garment. Likewise, the second, rear body panel 6 has an overall length, which is measured between opposed first and second terminal edges 14 and 18, and which is also less than the overall length of the absorbent garment. Each of the first and second body panels has an outboard edge 24, 28 formed along the outer periphery of laterally opposed side portions of the first and second body panel. It should be understood that the outboard edges of the front and rear body panels can be different lengths.

Referring to FIG. 1, one or more, and preferably a plurality, meaning two or more, laterally extending elastic elements 36 are secured to each of the first and second body panels. In one preferred embodiment, a plurality of laterally extending elastic elements are longitudinally spaced across substantially the entire length of the waist portion of the front and rear body panel 4,6, although they may be spaced across a lesser length. For example, elastic elements can extend along the upper waist portion and along the lower terminal edge defining in part a leg opening 120. In one embodiment, the front body panel has a "non-elasticized" area wherein there are no laterally extending elastic elements, or other elastic or elastomeric backing members, incorporated therein or making up any portion of the thickness or cross-section of the body panel at that area, such that the material can be gathered. It should be understood, that in an alternative embodiment, one or more separate waist bands, with or without elastic elements, can be secured to one or both of the rear and front body panels, preferably along the upper terminal edges thereof. In addition, one or both of the body panels can be formed without any elastic elements.

The front body panel preferably has a "deactivated" area 17 wherein the elastic elements are severed, chopped or otherwise deactivated, for example by using a rotary die cutter, by melt-breaking (e.g. with a heated or ultrasonic function roll) or by any other means know to those skilled in the art. In one preferred embodiment, the deactivated area 17 or landing zone is formed along a center portion of the front body panel and underlies a landing member 100 and a pair of fastener members. One or more leg elastic elements 38 can be secured along the inner terminal edges of the body panels 4, 6 and an absorbent composite 50 to form a gasket with the leg of the user.

The various waist and leg elastic elements can be formed from rubber or other elastomeric materials. One suitable material is a LYCRA® elastic material. For example, the various elastic elements can be formed of LYCRA® XA Spandex 540, 740 or 940 detex T-127 or T-128 elastics available from E.I. duPont De Nemours and Company, having an office in Wilmington, Del.

Each body panel is preferably formed as a composite, or laminate material, otherwise referred to as substrates or laminates, with the plurality of elastic strands sandwiched therebetween. Preferably two or more layers are bonded with various adhesives, such as hot melt, or by other techniques, including for example and without limitation ultrasonic bonding and heat pressure sealing. In one embodiment, the two layers are made of a non-woven material. It should be understood that the body panels can be made of a single layer or substrate of non-woven material, or can be comprised of more than two layers or substrates. Of course, it should be understood that other knitted or woven fabrics, non-woven fabrics, elastomeric materials, polymer films, laminates and the like can be used to form one or more of the body panel layers. The term "non-woven" web or material, as used herein, means a web having a structure of individual fibers or filaments that are interlaid, but not in an identifiable manner and without the aid of textile weaving or knitting, as in a knitted or woven fabric.

In one embodiment, the non-woven layers or substrates, and also a landing material 102, can be made by spunbonding. Spunbond nonwoven webs or materials are made from melt-spun filaments or spunbonded fibers which refers to small diameter fibers that are formed by extruding molten thermoplastic material as filaments from a plurality of fine, usually circular capillaries of a spinneret with the diameter of the extruded filaments then being rapidly reduced, for example, by non-eductive or eductive fluid-drawing or other well known spunbonding mechanisms. The production of spunbound nonwoven webs is described in U.S. Pat. No. 4,340,563 to Appel et al., U.S. Pat. No. 3,692,618 to Dorschner et al., U.S. Pat. No. 3,802,817 to Matsuki et al, U.S. Pat. No. 3,502,763 to Hartmann, U.S. Pat. No. 3,276,944 to Levy, U.S. Pat. No. 3,502,538 to Peterson, and U.S. Pat. No. 3,542,615 to Dodo et al, all of which are incorporated herein by reference. The melt-spun filaments formed by the spunbond process are generally continuous and have diameters larger than 7 microns, more particularly, between about 10 and 30 microns. Another frequently used expression of fiber or filament diameter is denier, which is defined as grams per 9000 meters of a fiber or filament. The fibers may also have shapes such as those described in U.S. Pat. No. 5,277,976 to Hogle, et al, U.S. Pat. No. 5,466,410 to Hills and U.S. Pat. Nos. 5,069,970 and 5,057,368 to Largman et al., all of which are incorporated herein by reference. The spunbond filaments usually are deposited, by one or more banks, onto a moving foraminous belt or forming wire where they form a web. Spunbonded filaments generally are not tacky when they are deposited onto the collecting surface.

Spunbond fabrics typically are stabilized or consolidated (pre-bonded) in some manner immediately as they are produced in order to give the web sufficient integrity to withstand the rigors of further processing into a finished product. This stabilization (prebonding) step may be accomplished through the use of an adhesive applied to the filaments as a liquid or powder which may be heat activated, or more commonly, by compaction rolls. As used herein, the term "compaction rolls" means a set of rollers above and below the web used to compact the web as a way of treating a just produced, melt-spun filament, particularly spunbond, web, in order to give the web sufficient integrity for further processing, but not the relatively strong bonding of secondary bonding processes, such as through-air bonding, thermal bonding, ultrasonic bonding and the like. Compaction rolls slightly squeeze the web in order to increase its self-adherence and thereby its integrity.

An alternative means for performing the pre-bonding step employs a hot air knife, as described in U.S. Pat. No. 5,707,468, the entirety of which is hereby incorporated herein by reference. Briefly, the term "hot air knife" means a process of pre-bonding a just produced melt-spun filament, particularly spunbond, web, in order to impart the web with sufficient integrity, i.e., increase the stiffness of the web, for further processing. A hot air knife is a device that focuses a stream of heated air at a very high flow rate, generally from about 300 to about 3000 meters per minute (m/min.), or more particularly from about 900 to about 1500 m/min., directed at the nonwoven web immediately after its formation. The air temperature usually is in the range of the melting point of at least one of the polymers used in the web, generally between about 90° C. and about 290° C. for the thermoplastic polymers commonly used in spunbonding. The control of air temperature, velocity, pressure, volume and other factors helps avoid damage to the web while increasing its integrity.

The hot air knife's focused stream of air is arranged and directed by at least one slot of about 3 to about 25 millimeters (mm) in width, particularly about 9.4 mm, serving as the exit for the heated air towards the web, with the slot running in a substantially cross-machine direction over substantially the entire width of the web. In other embodiments, there may be a plurality of slots arranged next to each other or separated by a slight gap. The at least one slot usually, but not necessarily, is continuous, and may be comprised of, for example, closely spaced holes. The hot air knife has a plenum to distribute and contain the heated air prior to its exiting the slot. The plenum pressure of the hot air knife usually is between about 2 to about 22 mmHg, and the hot air knife is positioned between about 6.35 mm and about 254 mm, and more particularly from about 19.05 to about 76.20 mm above the forming surface. In a particular embodiment, the hot air knife plenum's cross-sectional area for cross-directional flow (i.e., the plenum cross-sectional area in the machine direction) is at least twice the total slot exit area. Since the foraminous wire onto which spunbond polymer is formed generally moves at a high rate of speed, the time of exposure of any particular part of the web to the air discharge from the hot air knife typically is less than a tenth of a second and generally about one hundredth of a second, in contrast with the through-air bonding process, which has a much longer dwell time. The hot air knife process has a great range of variability and control over many factors, including air temperature, velocity, pressure, and volume, slot or hole arrangement, density and size, and the distance separating the hot air knife plenum and the web.

The spunbond process also can be used to form bicomponent spunbond nonwoven webs as, for example, from side-by-side (or sheath/core) linear low density polyethylene/polypropylene spunbond bicomponent filaments. A suitable process for forming such bicomponent spunbond nonwoven webs is described in U.S. Pat. No. 5,418,045 to Pike et al., which is incorporated herein by reference in its entirety.

Commercially available thermoplastic polymeric materials can be advantageously employed in making the fibers or filaments from which pattern-unbonded nonwoven material is formed. As used herein, the term "polymer" shall include, but is not limited to, homopolymers, copolymers, such as, for example, block, graft, random and alternating copolymers, terpolymers, etc., and blends and modifications thereof. Moreover, unless otherwise specially limited, the term "polymer" shall include all possible geometrical configurations of the material, including, without limitation, isotactic, syndiotactic and random symmetries. As used herein, the terms "thermoplastic polymer" or "thermoplastic polymeric material" refer to a long-chain polymer that softens when exposed to heat and returns to its original state when cooled to ambient temperature. Preferably, the spunbond fibers are made of a polypropylene. Other alternative thermoplastic materials include, without limitation, poly (vinyl chloride)s, polyesters, polyamides, polyfluorocarbons, polyolefins, polyurethanes, polystyrenes, polyethylenes, poly(vinyl alcohol)s, caprolactams, and copolymers of the foregoing. The fibers or filaments used in making the nonwoven material may have any suitable morphology and may include hollow or solid, straight or crimped, single component, bicomponent or multicomponent, biconstituent or multiconstituent fibers or filaments, and blends or mixes of such fibers and/or filaments, as are well known in the art.

After the nonwoven web is formed, the pre-bonded or unbonded web is passed through a suitable process or apparatus, including for example a calendar roll, to form a pattern of discrete bonded areas. The term "discrete" as used herein means individual or disconnected, and is contrasted with the term "continuous" as used in U.S. Pat. No. 5,858,515 to Stokes et al, the entirety of which is hereby incorporated herein by reference, and which describes pattern-unbonded, or point un-bonded, nonwoven fabrics having continuous bonded areas defining a plurality of discrete unbonded areas. In one embodiment, the calendar stack (not shown) includes an anvil roll and a pattern roll, which is heated and includes various raised landing portions. The raised portions of the pattern roll thermally bond the fibers to form the bonded areas. The bonds can made of any shape and size. Preferably, the percent bonded area of the web is between about 5% and 25% of the area of the web, and is more preferably between about 10% and 15%. Thereafter, the bonded substrate can be bonded to another substrate with the elastic members disposed therebetween.

In one alternative preferred embodiment, the landing material 102 is made of a point-unbonded nonwoven material, for example, a 2.0 osy point-unbonded material. One exemplary material of this type has been used in a HUGGIES® Ultratrim Disposable Diaper, which is commercially available from Kimberly-Clark Corporation. In another preferred embodiment, the landing material is made of a non-woven material, for example, a spunbond material having a basis weight of preferably about 0.6 osy. In other preferred embodiments, the basis weight of each substrate can be between at least about 0.3 and about 2.0 osy, and preferably between about 0.5 osy and about 1.5 osy, and more preferably between about 0.5 osy and about 1.0 osy. Even with a relatively low percent area bonding, the relatively low basis weight non-woven material exhibits strength and tear characteristics allowing it to be used as a body panel. Other materials that may be used as the non-woven material include various meltblown materials, and also bonded-carded materials.

In other alternative embodiments, the landing material can be made of a loop material, which typically includes a backing structure and a plurality of loop members extending upwardly therefrom. The loop material can be formed from any suitable material, such as acrylic, nylon or polyester, and can be formed by such methods as warp knitting, stitch bonding or needle punching. Suitable loop materials are available from Guilford Mills, Inc., Greensboro, N.C., U.S.A. under the trade designation No. 36549.

The body panel 4, 6 non-woven material is preferably substantially hydrophobic, which may optionally be treated with a surfactant or otherwise process to impart a desired level of wettability and hydrophilicity. In one particular embodiment of the invention, the body panel is a nonwoven, wire-weave spunbond polypropylene fabric composed of about 1.6 denier fibers formed into a web having a basis weight of about 0.6 osy. One suitable non-woven material is the Corinth 0.60 osy, 1.6 dpf wireweave, nonwettable Metallocene (EXXON ACHIEVE 2854 PP) spunbond material manufactured by Kimberly-Clark Corporation, the assignee of the present application.

Referring to FIG. 1, fastening members or tabs 42 are preferably attached to the front body panel and extend laterally inboard relative to the outboard side edge 24 of the front body panel 4 from an attachment location 45, which is preferably spaced inboard from the side edge. The front body panel 4 includes a middle portion 33, having a landing member 100 secured thereto, and opposite side portions 35. Opposite longitudinally extending lines of weakness 37 separate the middle portion 33 with the landing member 100 attached thereto, from the opposite side portions 35, such that the side portions 35 are initially breakably attached to opposite sides of the middle portion 33. The lines of weakness 37 can comprise a perforation or other series of cuts, a thinning, breakage or separation of material, or a strip of a different kind of material bridging between the middle portion and the side portions that is more easily torn or broken than the material of the middle portion and side portions, which allow a user or the manufacturer to separate the side portions from the middle portion. For example, the absorbent garment can be broken after the garment is applied to a user, or beforehand. Preferably, the fastening members 42 are secured to the garment-side surface of the side portions 35, preferably in a portion of the deactivated zone 17, between the side edge 24 of the front body panel and the line of weakness 37.

It should be understood that, in other embodiments, the fastening members can be secured to the rear body panel and engage the front body panel or, conversely, can be secured to the front body panel and engage the rear body panel, preferably along at least a portion that is not elasticized. Preferably, the fastening members are fixedly secured to the outer, garment-side surface of the front and/or rear body panels, and releasably engage the outer, garment-side surface of the front and/or rear body panels, although it should be understood that the fastening members could be fixedly secured to an inner body-side surface of front and/or rear body panels and releasably engage an inner, body-side surface of the front and/or rear body panels.

The opposite side edges 24 of the front body panel 4 are joined to the opposite side edges 28 of the rear body panel 6 to form a seam 39. The seam 39 is formed by bonding, sewing or otherwise attaching the side edges. In this way, prior to the breaking of the line of weakness 37, the absorbent garment can be configured as a pant-like garment, which can be pulled over the legs of the user. After the garment is applied to the user, the lines of weakness can be broken, if desired, or left intact, as the fasteners are adjusted to fit the garment to the user. If desired, the lines of weakness can be broken prior to securing the garment to the user, for example when the user is bed-ridden. In this configuration, the garment is laid beneath the user and is secured to the user with the fastening tabs. By providing the side portions, and by connecting the fastening tabs to the front panel, instead of the rear body panel, the tabs are located at the front of the user so as to not provide discomfort to the user when lying on their backs and to allow the fasteners to be more easily seen and adjusted by the user.

It should be understood that the lines of weaknesses and the fasteners can be moved laterally inboard and outboard to provide more or less adjustment capability. In addition, the elasticized side portions provide further adjustment capability.

It should be understood that the front and rear body panels can be made as a unitary member that extends along the crotch from the front to back and with the sides thereof connected to form side seams. Alternatively, the front and rear body panels can be formed integrally, for example as one panel extending around the waist and hips of the user.

In one alternative embodiment, an outer cover is disposed over the entire garment and forms the outer garment-side layer or substrate of the front and rear body panels, with the various elastic elements 36, 38 disposed between a bodyside liner on each of the front and rear body panels, which liner preferably is configured as a single substrate, and the outer cover, which is also preferably configured as single substrate. In this way, the portion of the outer cover that overlies the front body panel liner and is fitted around the front of the user forms part of the front body panel, while the portion of the outer cover that overlies the rear body panel liner and is fitted around the rear of the user forms part of the rear body panel. The front and rear body panels, with the liners and with the outer cover forming portions thereof and preferably extending therebetween, forms a chassis. The outer cover is preferably made of a non-woven material, similar to that of the other body panel materials described herein. It should be understood that the body panels, including the outer cover, can be configured with any number of a plurality of substrates, and that the body panels can include other layers and substrates.

Preferably, as shown in FIG. 1, the fastening members 42 comprise a carrier member 43 that is formed in a generally side-ways, "U" shape, with a vertical extending base member 55 and a pair of laterally extending and longitudinally spaced tab members 47. The carrier member could also comprise one or more than two tab members. The carrier members are preferably fixedly secured to the side portions of the front body panel 4 with adhesive bonds 49, sonic bonds, thermal bonds, pinning, stitching or other known types of attachment, as shown for example in FIG. 1. In alternative embodiments, the fastening members can be fixedly secured to the rear body panel or to one or both of the front and rear body panels, e.g., at the seam.

Each carrier member 43 has a longitudinal length and each of the tab members 47 comprises a refastenable portion or an engagement portion having a longitudinal length. The refastenable portion 51 preferably comprises an array of hooks, as explained below, but alternatively can comprise various adhesives, such as pressure sensitive adhesives, buttons, zippers, snaps and other releasable and reattachable fastening devices know to those skilled in the art.

Figure 2:
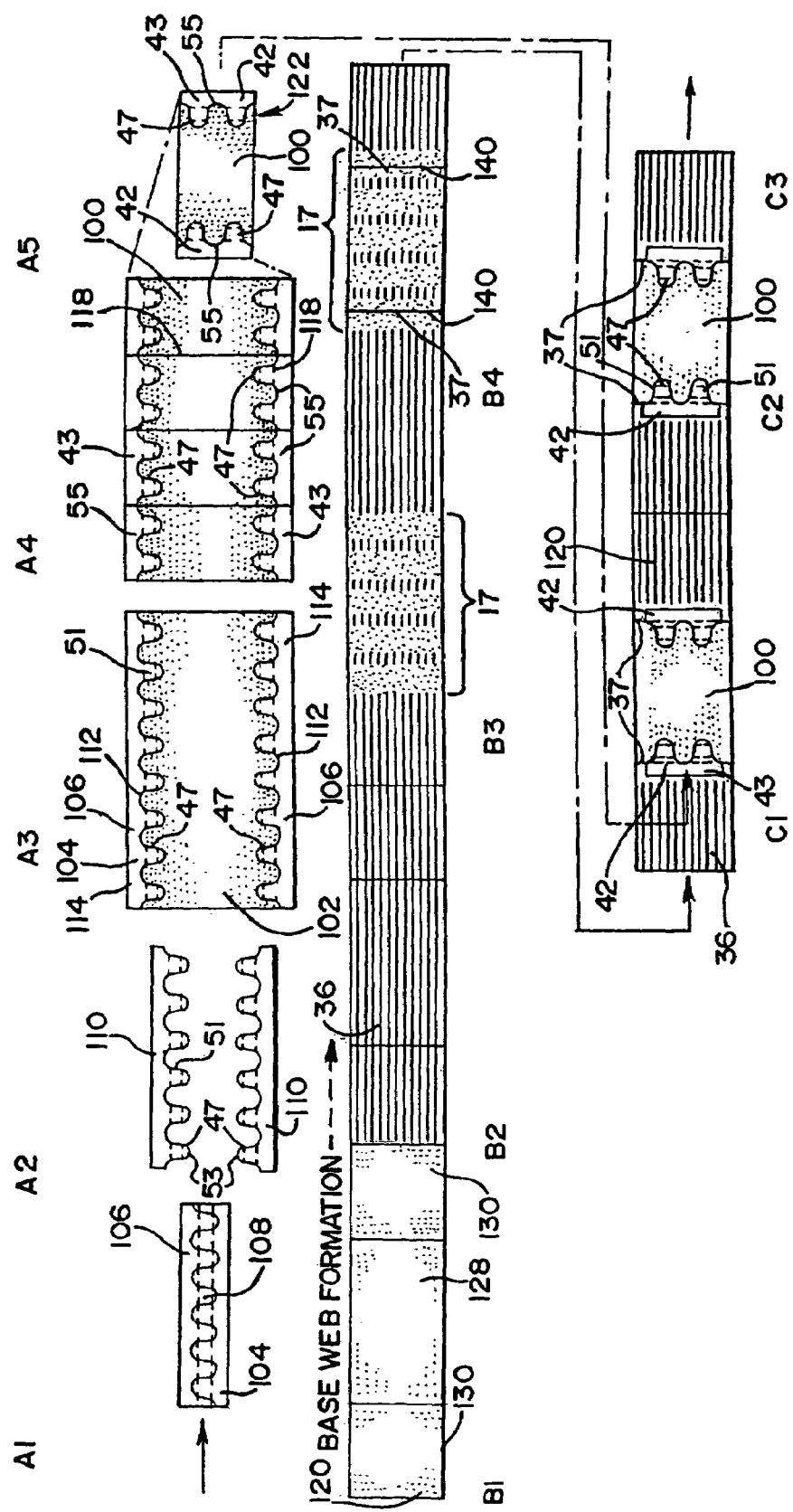
FIG. 2 is a schematic top view representation of a method of fabricating a front body panel of the refastenable absorbent garment.

In one embodiment, shown in FIGS. 1 and 2, each fastening member 42 is comprised of two separate, longitudinally spaced tab members 47. In any of the embodiments, the two or more tab members provides a pant-like fit that controls the waist and leg openings in the front and back of the garment, and also allows the user to adjust the fit of the garment without totally undoing the garment. For example, the user can release one of the tab members and refasten it without undoing the other tab member.

In one preferred embodiment, the refastenable portion 51 comprises a hook-type fastener member, or hook strip, which is secured to the carrier member 43 with adhesive, ultrasonic bonding, stitching or other known attachment devices. The end portion 53 or tip of the carrier member can be left uncovered by the refastenable portion 51, such that it can be lifted or flexed and grasped by a user as they disengage or peel back the fastener member. Alternatively, a portion of the array of hook members can be deadened, so as to provide an area that will not engage with the landing material and can thereby be grasped by the user. It should be understood that the term "hook" as used herein means any element capable of engaging another element, and is not intended to limit the form of the engaging elements, for example to include only "hooks," but rather encompasses any form or shape of engaging element, whether unidirectional or bi-directional. Various hook configurations are described in U.S. Pat. No. 5,845,375 to Miller et al., U.S. Pat. No. 6,132,660 to Kampfer, U.S. Pat. No. 6,000,106 to Kampfer, U.S. Pat. No. 5,868,987 to Kampfer, U.S. Pat. No. 4,894,060 to Nestegard, and U.S. Pat. No. 6,190,594 B1 to Gorman, the entire disclosures of which are incorporated by reference herein. Some examples of hook fasteners are the various CS600 hook fasteners, including the XKH-01-002 CS600, 2300 Pin Density hook fastener (Part No. XKH-01-002/60MM/SP#2628), manufactured by Minnesota Mining and Manufacturing Co., St. Paul Minn. Another example of a hook fastener is the Velcro® HTH-851 and HTH-829 hook fasteners available from Velcro USA, Inc.

In one preferred embodiment, a mushroom-type hook strip comprises a homogeneous backing of thermoplastic resin and, integral with backing, an array of upstanding stems distributed across at least one face of the backing, each having a mushroom head. The array of hooks on each strip comprise an engagement portion having a longitudinal length. The stems can have a molecular orientation as evidenced by a birefringence value of at least 0.001, and the mushroom heads having circular disc shapes with generally planar end surfaces opposite the backing, which disc shaped heads preferably have diameter to thickness ratios of greater than about 1.5 to 1.

The stems of the hook strip can be molecularly orientated as evidenced by a birefringence value of at least 0.001. As such, they have significantly greater stiffness and durability, as well as greater tensile and flexural strength, than would be achievable without such orientation. Because of these qualities, the portions of the stems not heated by a heating surface during the forming process remain resiliently flexible during a deforming step, which preferably involves the application of heat to the stem tips by contact with the heated surface of a metal roller. Such contact forms the tip of each stem into a circular disc shaped mushroom head at the tip of each stem, which head has a substantially flat inner surface that enhances its holding power when engaged with a loop.

As compared to hook strips that have unoriented stems, the enhanced strength of the hooks of the hook strip makes them less likely to break during disengagement. When the hook strip is used with the non-woven material herein described, the enhanced strength of the hooks makes them less likely to break under disengagement forces than the fibers of the material, a beneficial attribute for at least two reasons. First, broken hooks can create debris whereas a broken fiber typically does not. Furthermore, the non-woven material typically contains many more engageable fibers than there are hooks per unit area, thus allowing a greater number of disengagements before a hook-and-loop fastener becomes useless.

Although the stems of the hook strip preferably are generally circular in cross section, other suitable cross sections include rectangular and hexagonal. The stems preferably have fillets at their bases, both to enhance strength and stiffness and for easy release from a mold in which they are formed. In addition, the stems can be tapered, preferably from a larger to a smaller cross-section as one moves from the base to the head.

The stem portions are preferably at an angle of about 90 degrees from the backing substrate, however, this angle can range from about 80 to about 100 degrees, preferably 85 to about 95 degrees. The hook head portion is formed on the distal end of the stem. The hook head can be elongated in on or more directions forming the fiber engaging portions. These fiber engaging portions extend outward from the stem portion at any angle so that they can project upwardly away from the film backing, parallel with the film backing or even downward toward the film backing.

For example, the hook head portion has a deformed fiber engaging portion that projects downward. Preferably, the lower surface of the fiber engaging portion also projects downward form a crook between the lower face of the fiber engaging portion and the stem base portion. In one preferred embodiment, the heads of the hooks generally project at a downward angle from the hook head top portions toward the base. This downward angle (measured from a reference line taken from the top of the hook head and parallel with the backing) is generally from about 0 to about 70 degrees, preferably from about 5 to about 60 degrees and most preferably from about 5 to about 35 degrees (defined by a linear extent running from a center region of the hook head top portion to an end of the hook head fiber engaging portion).

The head shape with its high diameter to thickness ratio, and the small size and close spacing or high density of individual hooks that are provided by the hook strip according to the present invention makes it able to easily firmly releasably engage non-woven materials in shear, possibly because the many thin heads can easily move radially into engagement with rather small fibers. Thus the hook strip is particularly useful for hook-and-loop fastening when the "loops" are provided by non-woven materials which are not particularly adapted for use as the loop portions of hook and loop fasteners, and which are not as well engaged by known prior art hook strips. For example, the hook strip is particularly well-suited for engaging the topographically flatter non-woven materials described above, including the non-woven spunbond material, which has relatively fewer loose, outwardly extending, free fibers than conventional loop materials, but still provides a relatively high number of pores, of sufficient size, such that the material can be engaged by the hooks. Indeed, once the hooks are received in the pores, or embedded in the non-woven material, the fastening tabs provide excellent shear characteristics, such that the garment is securely fastened during normal wearing conditions.

In general, the hooks are of uniform height, preferably of from about 0.10 to 1.30 mm in height, and more preferably from about 0.18 to 0.51 mm in height; have a density on the backing preferably of from 60 to 1,600 hooks per square centimeter, and more preferably from 125 to 690 hooks per square centimeter, and preferably greater than about 150 hooks per square centimeter; have a stem diameter adjacent the heads of the hooks preferably of from 0.07 to 0.7 mm, and more preferably from about 0.1 to 0.3 mm. The deformed hook heads project radially past the stems on at least one side preferably by an average of about 0.01 to 0.3 mm, and more preferably by an average of about 0.02 to 0.25 mm and have average thicknesses between their outer and inner surfaces (i.e., measured in a direction parallel to the axis of the stems) preferably of from about 0.01 to 0.3 mm and more preferably of from about 0.02 mm to 0.1 mm. The hook heads have average head diameter (i.e., measured radially of the axis of the heads and stems) to average head thickness ratio preferably of from 1.5:1 to 12:1, and more preferably from 2.5:1 to 6:1.

For most hook-and-loop uses, the hooks of the hook strip should be distributed substantially uniformly over the entire area of the hook strip, usually in a square or hexagonal array.

To have both good flexibility and strength, the backing of the hook strip preferably is from 0.02 to 0.5 mm thick, and more preferably is from 0.06 to 0.3 mm in thick, especially when the hook strip is made of polypropylene or a copolymer of polypropylene and polyethylene. For some uses, a stiffer backing could be used, or the backing can be coated with a layer of pressure sensitive adhesive on its surfaces opposite the hooks by which the backing could be adhered to a substrate, such as the carrier member 43, so that the backing could then rely on the strength of the substrate to help anchor the hooks.

Virtually any orientable thermoplastic resin that is suitable for extrusion molding may be used to produce the hook strip. Thermoplastic resins that can be extrusion molded and should be useful include polyesters such as poly(ethylene terephthalate), polyamides such as nylon, poly(styrene-acrylonitrile), poly(acrylonitrile-butadiene-styrene), polyolefins such as polypropylene, and plasticized polyvinyl chloride. One preferred thermoplastic resin is a random copolymer of polypropylene and polyethylene containing 17.5% polyethylene and having a melt flow index of 30, that is available as SRD7-463 from Shell Oil Company, Houston, Tex.

The hook strip has preferably substantially continuous planar backing of thermoplastic resin. Integral with the backing is the array of hooks projecting generally at right angles to one major surface of the backing. Each of the hooks has a stem, and, at the end of the stem opposite the backing, a generally circular plate-like cap or head projecting radially past or overhanging the stem so as to form a fiber engaging portion that projects downward. Preferably, the lower surface of the fiber engaging portion also projects downward form a crook between the lower face of the fiber engaging portion and the stem base portion. The stem can also have a fillet around its base.

When the absorbent garment is secured to the user, the fastening tabs 42 secured to the side portions of the front body panels 4 releasably engage or are otherwise connected to the landing member secured to the middle portion of the front body panel 4. In particular, the heads on the hooks engage the fibers in the landing material.

Referring to FIGS. 1 and 4, the absorbent garment includes an absorbent composite 50 having first and second longitudinally opposed terminal end edges 60, 62. The absorbent composite preferably includes a substantially liquid permeable topsheet 64, or liner, and a substantially liquid impermeable backsheet 68, or outer cover. A retention portion 70 is disposed or sandwiched between the topsheet and the backsheet, which are connected. The topsheet, backsheet and other components of the absorbent composite 50 can be joined for example with adhesive bonds, sonic bonds, thermal bonds, pinning, stitching or any other attachment techniques known in the art, as well as combinations thereof. For example, a uniform continuous layer of adhesive, a patterned layer of adhesive, a sprayed pattern of adhesive or any array of lines, swirls or spots of construction bonds may be used to join the topsheet and backsheet, or any of the other components described herein. It should be understood that the term "absorbent composite" refers to any material or assembly capable of absorbing liquids or bodily exudates, and may be comprised of a single material or component, for example a retention portion.

Additional layers, including for example, a surge layer, are also preferably incorporated into the absorbent composite. Preferably, the surge layer does not run the entire length of the absorbent composite and is shorter than the retention portion. The topsheet can be indirectly joined to the backsheet by affixing the topsheet to intermediate layers, such as the surge layer or retention portion, which in turn is affixed to the backsheet. The absorbent composite also may include barrier cuffs, or leakage control shields, formed along the opposite longitudinally extending edges of the absorbent composite.

The backsheet 68 is preferably liquid impermeable, but may be liquid permeable, e.g., when an additional barrier layer is used with the retention portion. For example, in one embodiment, the backsheet can be made from a thin plastic film, or other flexible, substantially liquid-impermeable material. As used herein, the term "flexible" means a material that is compliant and which will readily conform to the general shape and contour of the body of the user. The backsheet prevents various bodily fluids and exudates from wetting or otherwise contaminating various bedding or outer garments worn by the user over the absorbent garment. In particular, the backsheet can include a film, such as a polyethylene film, having a thickness of from about 0.012 mm to about 0.051 mm.

In various constructions, the topsheet can comprise various woven or nonwoven materials. For example, the topsheet can be composed of a meltblown or spunbonded web of desired fibers, and may also be a bonded-carded web. For example, the topsheet can be made of a substantially hydrophobic material, and the hydrophobic material may optionally be treated with a surfactant or otherwise processed to import a desired level of wettability and hydrophilicity. In one particular embodiment of the invention, the topsheet is a nonwoven, spunbond polypropylene fabric composed of about 2.8–3.2 denier fibers formed into a web having a basis weight of about 22 gsm and density of about 0.06 gm/cc. The fabric can be surface treated with an operative amount of surfactant, such as about 0.28% Triton X-102 surfactant. The surfactant can be applied by any conventional means, such as spraying, printing, brush coating or the like.

In various constructions, the backsheet can comprise a woven or nonwoven fibrous web layer, which is treated or constructed, partially or wholly, to impart the desired levels of liquid impermeability to selected regions that are adjacent to or proximate the absorbent retention portion. For example, the backsheet may include a gas-permeable, nonwoven fabric layer laminated to a polymer film layer which may or may not be gas-permeable. Other examples of fibrous, cloth-like backsheet materials can comprise a stretch thinned or stretch thermal laminate material composed of a 0.6 mil (0.015 mm) thick polypropylene cast film and a 0.7 ounce per square yard (23.8 gsm) polypropylene spunbond material (2 denier fibers). A material of this type has been employed to form the outercover of a HUGGIES® Ultratrim Disposable Diaper, which has been commercially available from Kimberly-Clark Corporation. The backsheet can provide the outercover of the article, particularly in the crotch region. Optionally, however, the article may include a separate outercover component member, as disclosed herein, which is additional to the backsheet. The outercover can be joined, for example, to one or more of the absorbent composite and/or body panels as explained above.

The backsheet may include a micro-porous, "breathable" material which permits gases, such as water vapor, to escape from the absorbent garment while substantially preventing liquid exudates from passing through the backsheet. For example, the breathable backsheet may be composed of a microporous polymer film or a nonwoven fabric which has been coated or otherwise modified to impart a desired level of liquid impermeability. For example, a suitable microporous film can be a PMP-1 material, which is available from Mitsui Toatsu Chemicals, Inc., a company having offices in Tokyo, Japan; or an XKO-8044 polyolefin film available from 3M Company of Minneapolis, Minn. The backsheet may also be embossed or otherwise provided with a pattern or matte finish to exhibit a more aesthetically pleasing appearance.

In various configurations of the invention, where a component, such as the backsheet is configured to be permeable to gas while having a resistance and limited permeability to aqueous liquid, the liquid resistant component can have a construction which is capable of supporting a selected hydrohead of water substantially without leakage therethrough. A suitable technique for determining the resistance of a material to liquid penetration is Federal Test Method Standard FTMS 191 Method 5514, 1978, or an equivalent thereof.

In one preferred embodiment, the backsheet is sufficiently impermeable to liquid and semi-liquid materials to substantially prevent the undesired leakage of waste materials, defined as exudates, including for example urine and feces. For example, the backsheet member can desirably support a hydrohead of at least about 45 centimeters (cm) substantially without leakage. The backsheet member can alternatively support a hydrohead of at least about 55 cm, and optionally, can support a hydrohead of at least about 60 cm, or more, to provide improved benefits.

The backsheet and/or outercover also can be extensible. In one preferred embodiment, the backsheet and/or outercover is capable of providing an elongation of at least about 1 cm when subjected to a tensile force of 11.8 g/cm, and further provides a substantially permanent deformation of at least about 20% when subjected to a tensile force of 19.70 g/cm and is then allowed to relax under a zero applied stress for a period of 1 minute.

For example, the extensible member can be composed of a necked fiber, a creped fiber, a micro-pleated fiber, polymer films or the like, as well as combinations thereof. The fabrics may be woven or nonwoven materials, such as spunbond fabrics. One example of a suitable extensible material is a 60% necked, polypropylene spunbond having a basis weight of about 1.2 osy.

The backsheet and/or outercover also can be expandable, for example when it has one or more folds, e.g., one or more z-folds (not shown), or can be both extensible and expandable. The term expandable as used herein means to enlarge or to increase the extent or area, lateral and/or longitudinal, thereof, e.g., by unfolding one or more folds.

The retention portion 70 is preferably made of an absorbent material, which can be any material that tends to swell or expand as it absorbs exudates, including various liquids and/or fluids excreted or exuded by the user. For example, the absorbent material can be made of airformed, airlaid and/or wetlaid composites of fibers and high absorbency materials, referred to as superabsorbents. Superabsorbents typically are made of polyacrylic acids, such as FAVOR 880 available from Stockhausen, Inc. of Greensboro, N.C. The fibers can be fluff pulp materials, such as Alliance CR-1654, or any combination of crosslinked pulps, hardwood, softwood, and synthetic fibers. Airlaid and wetlaid structures typically include binding agents, which are used to stabilize the structure. In addition, various foams, absorbent films, and superabsorbent fabrics can be used as an absorbent material. Various acceptable absorbent materials are disclosed in U.S. Pat. No. 5,147,343 for Absorbent Products Containing Hydrogels With Ability To Swell Against Pressure, U.S. Pat. No. 5,601,542 for Absorbent Composite, and U.S. Pat. No. 5,651,862 for Wet Formed Absorbent Composite, all of which are hereby incorporated herein by reference. Furthermore, the proportion of high-absorbency particles can range from about 0 to about 100%, and the proportion of fibrous material from about 0 to about 100%. Additionally, high absorbency fibers can be used such as Oasis type 121 and type 122 superabsorbent fibers available from Technical Absorbent Ltd., Grimsby, Lincolnshire, United Kingdom.

The retention portion 70 has laterally opposed side edges 74 and preferably can be made of a single or dual layer of absorbent material. The retention portion preferably has an hour-glass shape with enlarged end regions. Alternatively, the retention portion can include a folded or multi-layered configuration. The retention portion preferably has a length substantially equal to, or slightly shorter than, the length of the absorbent composite. The retention portion can include one or more barrier layers attached to the absorbent material. In one embodiment, an upper tissue substrate is disposed adjacent the retention portion. Alternatively, a lower tissue substrate can be disposed adjacent an opposite side of the retention portion, or the tissue can completely envelope the retention position.

Referring to FIG. 1, the opposite garment side of the end regions of the absorbent composite, and in particular, the outer, garment side surface of the backsheet 68, are secured to the bodyside surface of the longitudinally opposed crotch ends of the first and second body panels 4, 6. It should be understood that the absorbent composite can be secured using any of the methods of attachment described above, including for example various adhesives, stitching or other bonding methods. The absorbent composite can be secured to the body panels with any configuration of attachment lines, swirls, patterns, spots, etc., or can be a full and continuous attachment therebetween.

Figure 3:
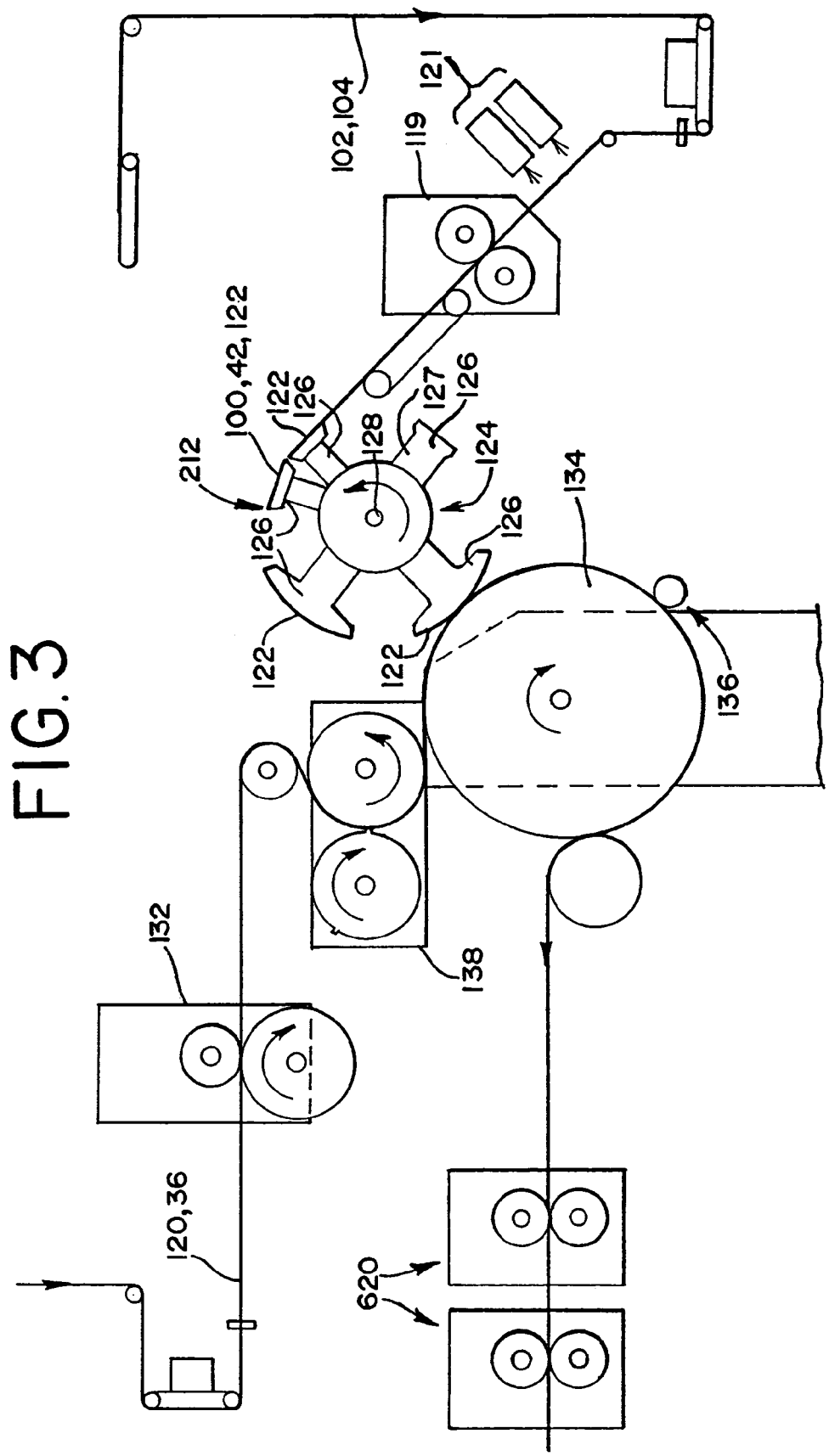
FIG. 3 is a schematic side view representation of an apparatus for and method of fabricating the front body panel.

Referring to FIGS. 2–4, the method and apparatus for fabricating one or more embodiments of the aforedescribed refastenable absorbent garment is illustrated. Although the process is described in terms of various zones, it should be understood that it is a continuous process.

Referring to FIG. 2 at zone A1, a roll of fastener material 104 provides a continuous supply or strip of fastener material moving in a machine direction and having a carrier material 106 forming outer lateral base portions and an engagement material 108 disposed along a middle portion of the carrier material to form the refastenable portion. The strip of fastener material is cut along the machine direction, preferably in a serpentine cut, to form a pair of strips 110 of fastener material, each having a plurality of tab members 47 facing laterally inward toward the other strip of fastener material. The strips can be cut using a rotary die cutter. Referring to zone A2, the strips of fastener material are separated such that they are laterally spaced in the cross direction. The strips 110 are also aligned, with one or both of the strips being moved in the machine direction relative to the other, such that the tab members 47 are aligned in the cross direction directly opposite each other. For example, U.S. Pat. No. 5,540,796, entitled Process for Assembling Elasticized Ear Portions and assigned to Kimberly-Clark Corporation, the entire disclosure of which is hereby incorporated herein by reference, discloses one embodiment of the cutting, separating, and aligning process.

Referring to zone A3, a continuous web of landing material 102 is introduced into the process and moves therealong in a machine direction. The landing material 102 can be made of any of the above-described materials, including for example a point unbonded, nonwoven material or a spunbond nonwoven material. The landing material can also be made of various known loop materials. Alternatively, if the fastener member is configured as a tape, the landing material preferably made of various known materials that interface with such tape. The landing material has opposite lateral side edges 112. The pair of strips 110 of fastener material are applied to the landing material along the opposite side edges 112.

In a preferred embodiment, the refastenable portion 51 of the fastener material is removeably or releasably engaged with the landing material 102. For example, in one preferred embodiment, the refastenable portion 51 of the fastener material comprises a hook material that is embedded in the landing material 102. In another embodiment, the refastenable portion comprises a tape or adhesive that is engaged with the landing material. Preferably, the base portion 114, or at least a portion thereof, of the fastener material extends laterally outboard or outwardly beyond the opposite side edges 112 of the landing material. It should be understood that the fastener material can be comprised of a single material that forms both the base portion and the refastenable portion, and that the term "base portion" is meant to refer to that portion of the fastener material that is secured to the front panel 4 on the outboard side of the line of weakness 37, preferably in a nonremovable relationship thereto. Preferably, engagement between the refastenable portion of the fastener material and the landing material, whether it be of a hook and loop engagement or an adhesive engagement, is the only type of engagement between those two members. In one embodiment, a nip can be used to facilitate the engagement between the refastenable portion and the landing material. Of course, it should be understood that the fastener material could be otherwise secured to the landing material by a device other than the refastenable portion, for example by using additional bonds or adhesives that can be broken when the garment is in use.

Referring to FIG. 3 and zone A4 of FIG. 2, the landing material 102, with the fastener material 104 removeably secured thereto by way of the engagement between the refastenable portion and the landing material, is successively cut along the cross direction to form a plurality of discrete landing members 100, each having a pair of fastener members 42 secured to the opposite side edges thereof. As shown in FIG. 3, for example, a perforation cut 118 can be made with a cutter 119. An adhesive applicator 121 can apply an adhesive to the body side surface of the landing material upstream of the cutter 119, as shown in FIG. 3, or downstream thereof after the landing members have been formed and defined. The cut alternatively can be a continuous cut, e.g. a slit, so as to completely separate successive landing members and fastener members, which preferably are carried on a conveyor, or it can be a perforation cut. Preferably, the cuts are made such that each fastener member 42 is formed with two tab members 47 having a pair of refastenable portions 51. Of course, it should be understood that the cuts can be spaced such that the fastener member has a single tab member, or more than two tab members.

Referring to FIGS. 2 and 3, and in particular zone A5, each of the landing members 100 and fastener members 42, whether separated completely from the next successive landing member and fastener members, or partially connected thereto by way of a perforation, is rotated and accelerated and applied to a body panel base web 120 moving along in the process in a machine direction. In one alternative embodiment, the rotator cuts the landing material and fastener material and separates the resultant landing members and fastener members. The base web is preferably moving at a greater speed than the landing material. The base web is made of one or more of the materials described above with respect to the body panels and preferably is made of a spunbond nonwoven material. The landing member 100, which is preferably elongated in the cross direction prior to rotation, is rotated such that it is elongated in the machine direction, with the opposite pairs of fastener members 42 forming the leading and trailing edge of a refastenable subassembly 122, which is comprised of a landing member 100 and a pair of fastener members 42, as it travels in the machine direction.

As shown in FIG. 3, the refastenable subassembly is rotated using an offset cam action rotator 124. The rotator includes a plurality of transfer segments 126, which can have a vacuum applied thereto, that engage the refastenable subassembly 122. Coupler arms 127 connect the transfer segments and a drive ring. The coupler arm 127 includes a cam end having a cam follower that follows the profile of a cam mechanism. The profile of the cam mechanism can be readily changed to change the desired speed output and pitch of the fastener members. Preferably, the landing material, with the fastener material removeably secured thereto, or the stream of refastenable subassemblies, are moving at a slower speed than the speed of the body panel web. The rotator is configured to accelerate the refastenable subassemblies. If the successive subassemblies 122 are separated by a perforation, the transfer segment 126 breaks the perforation as it engages the subassembly and moves away from the next subassembly 122, which is engaged by a next transfer segment 126. The rotator rotates the end portion of the transfer segment, preferably approximately 90 degrees, about a radial axis, such that the subassembly is oriented in the machine direction as described above as the transfer segments are rotated about a horizontal axis 128. Alternatively, the landing material and fastener material are cut and separated by the transfer segments. The rotator, and the method for the use thereof, is further disclosed in U.S. Pat. Nos. 5,761,478, 5,759,340, and 6,139,004, all of which are assigned to Kimberly-Clark Worldwide, Inc., the assignee of the present application, and the entire disclosures of all of which are hereby incorporated herein by reference. Alternatively, the subassembly can be rotated using a revolving transfer roll as shown and described in U.S. Pat. No. 4,608,115, which is assigned to Kimberly-Clark Worldwide, Inc., the assignee of the present application, and which is hereby incorporated herein by reference in its entirety.

Referring to FIG. 2, the base web, which preferably forms the front body panel, and which is preferably made of one or more of the materials described above, is moved along in the process in the machine direction. At zone B1, an adhesive is applied to one side of the base web. Preferably, the adhesive is applied as a continuous adhesive layer, or intermittently as a continuous adhesive layer 128 and a microbead adhesive layer 130. Alternatively, the adhesive can be applied intermittently, with ultrasonic bonds connecting the substrates in the regions between the application of adhesive. The adhesive is preferably applied intermittently only when a landing member is being applied over the area of no adhesive or the area of microbead adhesive, which areas also preferably include deadened elastic elements.

Referring to FIG. 2 (zone B2), the plurality of elastic elements 36 are applied between a body panel base web 120 liner and an outer base web layer with an elastic applicator in one or more of the configurations described above. The body panel web 148 shown in FIG. 4 can be fabricated in a similar fashion. The outer base web layer, which can be formed from the outer cover, is adhered to the liner with the adhesive, or with other known devices such as ultrasonic bonds, thermal bonds, stitching and the like. For example, as shown in FIG. 1, the elastic elements are applied in the machine direction as they are spaced across the entire length (defined in the cross direction) of the waist portion of the body panel base web. In particular, the elastic elements are applied between two substrates of the base web, e.g., a front body panel liner substrate and an outer cover substrate. At the same time, elastic elements are applied to another base web 148, e.g., the rear body panel, running parallel to the first base panel. The body panel web, with the elastic elements disposed between the two substrates, is passed through a nip. Various aspects for fabricating the absorbent garment, and for introducing the elastic elements, are shown and described in U.S. Pat. No. 5,643,396, which is hereby incorporated herein by reference.

Referring to FIGS. 2 and 3, and in particular zone B3, the elastic elements 36 are deactivated in the landing zone 17 with a timed elastic cutter 132, preferably by severing or chopping the elastic elements. In zone B4, a pair of machine direction spaced cross direction cuts 140 are made in the base web with a cutter 138 to form the lines of weakness 37, preferably in the landing zone and preferably spaced inwardly from the outboard edges of the landing zone. The cutter can be a knife and anvil cutter, or a laser, water jet or other type of cutter known to those of skill in the art.

Referring to FIGS. 2 and 3, and in particular zone C1, the refastenable subassembly 122 is applied to the base web with the rotator 124 as the base web 120 wraps around a construction drum 134. In particular, the landing member 100 is applied to the base web 120 in the landing zone 17 between the lines of weakness 37, or perforation cuts 140. The landing member 100 is held to the base web 120 with adhesive, which is applied to the landing member, or landing material if not cut, by applicator 121. At the same time the landing member 100 is being applied to the base web, the base portion 55 of the fastener members, or that portion of the fastener member extending beyond the side edge of the landing member, are secured to the base web 120, preferably in the landing zone 17, with the base portion 55 also being adhered to the base web with adhesive, which was previously applied thereto. The base portion 55 is applied to the base web 120 on the opposite side of the line of weakness 37 that the landing member 100 is applied, such that the fastener member 42 spans the line of weakness 37. The base web 120, with the subassembly 122 applied thereto, passes through a nip 136, which further bonds the subassembly to the base web.

Referring to FIG. 3, the fastener members 42, once applied to the body panel base web 120 with the rotator 124, are preferably bonded to the body panel web using one or more, and preferably two, bonders 620, and preferably ultrasonic bonders. An exemplary ultrasonic bonder is the rotating horn and anvil type ultrasonic bonder disclosed in U.S. Pat. No. 5,660,679, the entirety of which is hereby incorporated herein by reference. Another type of ultrasonic bonder is disclosed in U.S. Pat. No. 6,123,792, the entire disclosure of which is hereby incorporated herein by reference. It should be understood that the fastener members can be secured to the body panel webs with other adhesives, stitching, and/or other types of attachment known to those of skill in the art.

Referring to FIG. 4, and in particular, zone D1, the base web 120 is further secured to the absorbent composite 50, which is also secured to a base web 148 that forms the rear body panel. In particular, the front panel base web 120 moves along a path parallel to the back panel base web 148 in machine direction. The absorbent composite 50, extending in the cross direction, is then applied to the bodyside of each of the front and rear body panel base webs 120, 148 to form a ladder type configuration, although it should be understood that the absorbent composite could be attached to the garment side of each body panel. The absorbent composite 50 is secured to the body panel base webs 120, 148 by bonding and the like, or by other devices known to those of skill in the art.

In an alternative embodiment, an outer cover can be secured to one or more body panel liners and form part of the front and rear body panels and a crotch portion of the absorbent garment. In this embodiment, a die cutter cuts leg openings in the outer cover between the absorbent composites, and can also be configured to further define the shapes of the body panels.

At zone D2, the absorbent composite 50 is folded such that the rear body panel base web 148 overlies and faces the front body panel base web 120. Side seams 39 are formed with a side seal bonder, preferably by ultrasonic bonding, or with adhesive bonds, stitching or other suitable means known to those skilled in the art. At zone D3, a cross direction cut 150 is made through the side seam to separate the refastenable absorbent garments. The cut can be made with a knife and anvil.

Various aspects of the process for making the absorbent garment are further disclosed in U.S. application Ser. No. 09/834,870, filed Apr. 13, 2001, and entitled "Multiple Component Web," U.S. application Ser. No. 09/834,875, filed Apr. 13, 2001 and entitled "Method of Assembling Personal Care Absorbent Article," U.S. application Ser. No. 09/834,869, filed Apr. 13, 2001, and entitled "Pant-Type Personal Care Articles, and Methods of Making and Using Such Personal Care Articles," U.S. application Ser. No. 09/834,787, filed Apr. 13, 2001 and entitled "Methods of Changing Size of Pant-Type Personal Care Articles Outputted from a Manufacturing Process," and U.S. application Ser. No. 09/834,682, filed Apr. 13, 2001 and entitled "Passive Bonds For Personal Care Article," the entire disclosures of which are hereby incorporated by reference.

In other aspects, the absorbent garment and the process for making the absorbent garment are further disclosed in U.S. Provisional Application Serial No. 60/303,307, filed Jul. 5, 2001, and entitled "Refastenable Absorbent Garment," the entire disclosure of which is hereby incorporated by reference.

Although the present invention has been described with reference to preferred embodiments, those skilled in the art will recognize that changes may be made in form and detail without departing from the spirit and scope of the invention. As such, it is intended that the foregoing detailed description be regarded as illustrative rather than limiting and that it is the appended claims, including all equivalents thereof, which are intended to define the scope of the invention.

What is claimed is:

1. An apparatus for fabricating a refastenable absorbent garment comprising a base web having a plurality of elastic members, a piece of landing material attached to the base web and a fastener member removeably attached to the piece of landing material and fixedly attached to the base web, the apparatus comprising:

a web perforator adapted to perforate the base web in a cross direction;

a construction drum positioned downstream of said web perforator and adapted to receive the perforated base web;

a landing material cutter adapted to cut a landing material and a fastener material in the cross direction and thereby form a plurality of the pieces of landing material with a plurality of the fastener members secured thereto respectively; and a landing member rotator positioned adjacent said construction drum and downstream of said landing material cutter, wherein said landing member rotator is adapted to separate successive pieces of landing material with the fastener members attached thereto at the cross direction landing material cut, rotate the piece of landing material with the fastener member attached thereto and apply the piece of landing material and the fastener member to the base web on the construction drum.

2. The apparatus of claim 1 further comprising an elastic deactivator positioned upstream of said web perforator and adapted to deactivate at least a portion of the plurality of elastic members.

3. The apparatus of claim 1 wherein said landing material cutter comprises a perforator.

4. The apparatus of claim 1 further comprising a nip positioned downstream of said landing member rotator, said nip adapted to bond the piece of landing material to the base web.

5. The apparatus of claim 4 wherein said nip is formed in part by said construction drum.

6. The apparatus of claim 1 further comprising a bonder positioned downstream of said construction drum, wherein said bonder is adapted to fixedly secure the fastener member to said base web.

7. The apparatus of claim 6 wherein said bonder comprises an ultrasonic bonder.

8. The apparatus of claim 1 further comprising an adhesive applicator positioned upstream of said landing member rotator, said adhesive applicator adapted to apply an adhesive to the landing material.

9. The apparatus of claim 8 wherein said adhesive applicator is positioned upstream of said landing material cutter.

10. The apparatus of claim 1 wherein said rotator comprises a cam action rotator.

11. An apparatus for fabricating a refastenable absorbent garment comprising a base web having a plurality of elastic members, a piece of landing material attached to the base web and a fastener member removeably attached to the piece of landing material and fixedly attached to the base web, the apparatus comprising:
- a web perforator adapted to perforate the base web in a cross direction;
- a construction drum positioned downstream of said web perforator and adapted to receive the perforated base web;
- a landing material cutter adapted to cut a landing material and a fastener material in the cross direction and thereby form a plurality of the pieces of landing material with a plurality of the pieces of fastener members secured thereto;
- a landing member rotator positioned adjacent said construction drum and downstream of said landing material cutter, wherein said landing member rotator is adapted to separate successive pieces of landing material with the fastener members attached thereto at the cross direction landing material cut, rotate the piece of landing material with the fastener member attached thereto and apply the piece of landing material and the fastener member to the base web on the construction drum;
- an adhesive applicator positioned upstream of said landing member rotator, said adhesive applicator adapted to apply an adhesive to the landing material; and
- a bonder positioned downstream of said construction drum, wherein said bonder is adapted to fixedly secure the fastener member to said base web.

12. The apparatus of claim 11 further comprising an elastic deactivator positioned upstream of said web perforator and adapted to deactivate at least a portion of the plurality of elastic members.

13. The apparatus of claim 11 wherein said landing material cutter comprises a perforator.

14. The apparatus of claim 11 further comprising a nip positioned downstream of said landing member rotator, said nip adapted to bond the piece of landing material to the base web.

15. The apparatus of claim 14 wherein said nip is formed in part by said construction drum.

16. The apparatus of claim 11 wherein said bonder comprises an ultrasonic bonder.

17. The apparatus of claim 11 wherein said adhesive applicator is positioned upstream of said landing material cutter.

18. The apparatus of claim 11 wherein said rotator comprises a cam action rotator.

* * * * *